United States Patent [19]

Parrinello et al.

[11] Patent Number: 5,134,234
[45] Date of Patent: Jul. 28, 1992

[54] IMINOSILANES

[75] Inventors: Giovanni Parrinello, Duisburg, Belgium; Rolf Mühaupt, Freiburg, Fed. Rep. of Germany

[73] Assignee: CIBA-GEIGY Corporation, Ardsley, N.Y.

[21] Appl. No.: 566,960

[22] Filed: Aug. 14, 1990

[30] Foreign Application Priority Data

Aug. 24, 1989 [CH] Switzerland .................. 3069/89

[51] Int. Cl.$^5$ ............... C07D 251/32; C07F 7/04; C07F 7/10
[52] U.S. Cl. .......................... 544/221; 556/420
[58] Field of Search .................. 556/420; 544/221

[56] References Cited

U.S. PATENT DOCUMENTS 4,853,454  8/1989  Merger et al. .............. 556/420

FOREIGN PATENT DOCUMENTS 3414877  10/1985  Fed. Rep. of Germany .

OTHER PUBLICATIONS

M. Bock et al., J. Coatings Tech. 59, 131 (1987).

Primary Examiner—Johann Richter
Attorney, Agent, or Firm—Luther A. R. Hall

[57] ABSTRACT

Novel iminosilanes of the general formula Ia or Ib

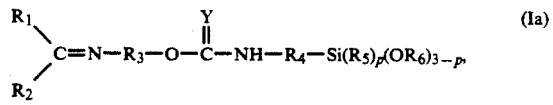

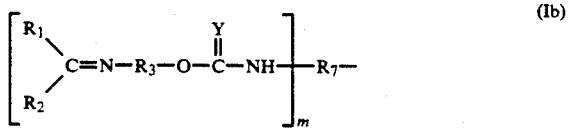

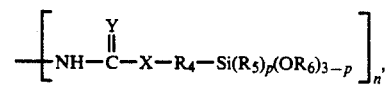

in which $R_1$ is alkyl, cycloalkyl or aralkyl containing at least on the α-C atom substituents which are inert towards isocyanate groups, so that no hydrogen atom is present on this C atom, $R_2$ is as defined for $R_1$ or is hydrogen, or $R_1$ and $R_2$, together with the common C atom, form a cyclohexylene ring which has on the two C atoms substituents which are inert towards isocyanate groups, $R_3$ to $R_7$ are organic radicals, p is 0,1 or 2, m is 1 or 2, n is an integer from 1 to 5 and X is —S— or —NH—, are described.

11 Claims, No Drawings

IMINOSILANES

The present invention relates to novel iminosilanes, curable compositions containing polyisocyanates and these silanes, the cured products obtainable therefrom and the use of the novel compounds for the preparation of coverings, adhesives and coatings.

The use of iminosilanes as adhesion promoters in curable polyurethane compositions which are suitable for sticking glass is known per se. Thus, for example, polyurethane preparations which contain an incorporated adhesion promoter based on alkoxysilanes containing aldimine or ketimine groups are described in DE-A-3,414,877. With these one-component polyurethane compositions which can be employed without a primer can be prepared. The adhesion promoters disclosed are derived from aldehydes containing hydrogen atoms on the C atom in the α-position relative to the aldehyde group.

Polyurethane curing agents based on aldimines are described in DE-3,624,924. The compounds are derived from aldehydes which contain no hydrogen atoms on the C atom in the α-position relative to the aldehyde group. The compounds contain no silane groups and as a rule have no adhesion-promoting properties.

Selected iminosilanes which can be employed as adhesion promoters have now been found. Storage-stable polyurethane compositions which can be cured rapidly under the influence of moisture and have very good adhesion properties on a number of substrates, in particular on glass surfaces, can be prepared using these iminosilanes. An acceleration in the curing reaction is found here, this being particularly pronounced with the polyfunctional iminosilanes.

This is to be regarded as surprising, since the adhesion of the cured product usually leaves something to be desired if the curing speed is high.

The present invention relates to compounds of the general formula Ia or Ib

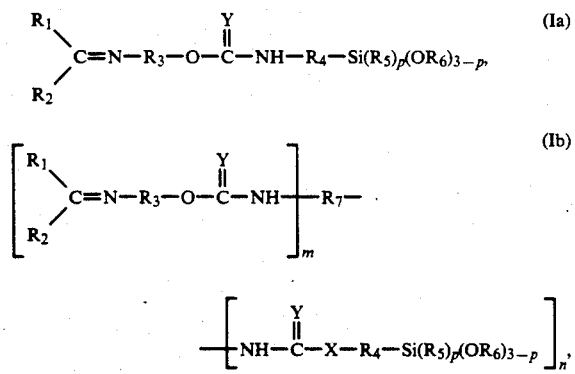

in which $R_1$ is alkyl, cycloalkyl or aralkyl containing at least on the α-C atom substituents which are inert towards isocyanate groups, so that no hydrogen atom is present on this C atom, $R_2$ is as defined for $R_1$ or is hydrogen, $R_1$ and $R_2$, together with the common C atom, form a cyclohexylene ring which contains on the two C atoms substituents which are inert towards isocyanate groups, $R_3$ is alkylene or cycloalkylene, Y is —O— or —S—, $R_4$ is alkylene or cycloalkylene, $R_5$ is alkyl, alkenyl, cycloalkyl, aryl or aralkyl, $R_6$ is alkyl or cycloalkyl, or two radicals $R_6$ together can also form an alkylene chain, p is 0, 1 or 2, m is 1 or 2, n is an integer from 1 to 5, $R_7$ is an m+n-valent linear or branched radical of a polyisocyanate after removal of the isocyanate groups and X is —S— or —NH—, and in which the radicals $R_3$ to $R_7$ independently of one another either are unsubstituted or contain substituents which are inert towards isocyanate groups, and in which, in alkyl radicals $R_1$, $R_2$, $R_5$ and/or $R_6$ and/or in alkylene radicals $R_3$, $R_4$ and/or $R_7$, one or more carbon atoms can be replaced by oxygen atoms, so that polyalkylene glycol radicals occur, and in which, in cyclic radicals $R_1$ to $R_7$, one to three carbon atoms can be replaced by oxygen atoms, sulfur atoms and/or nitrogen atoms.

Any alkyl radicals $R_1$ or $R_2$ contain at least on the α-C atom two, in particular in total two to four, substituents which are inert towards isocyanate groups, such as alkyl groups.

These radicals are preferably those of the formula II

in which $R_8$ and $R_9$ are identical or different $C_1$–$C_6$alkyl and $R_{10}$ is $C_1$–$C_{12}$alkyl, or $R_{10}$ is one of the radicals of the formulae IIIa, IIIb or IIIc

in which $R_{11}$ is $C_1$–$C_{12}$alkyl, cyclohexyl, phenyl or benzyl.

Examples of suitable radicals $R_1$ and $R_2$ are tert-butyl, 1,1,3,3-tetramethylpentyl, 1-(n-butoxy)-1-methylethyl, 1-(2-ethylhexyloxy)-1-methylethyl, 1-(methoxycarbonyl)-1-methylethyl and 1-(methylcarbonyloxy)-1-methylethyl. tert-Butyl is preferred.

Any cycloalkyl radicals $R_1$ or $R_2$ are in all cases substituted at least on the α-C atoms, for example by alkyl. An example of these cycloalkyl radicals is 1-methylcyclohex-1-yl.

An example of a cyclohexylene ring which is formed by $R_1$ and $R_2$ together with the common C atom and contains on the two C atoms substituents which are inert towards isocyanate groups is 2,2,6,6-tetramethylcyclohexyl.

Any aralkyl radicals $R_1$ or $R_2$ are as a rule radicals which have seven to twelve carbon atoms and are substituted at least on the α-C atom by radicals which are inert towards isocyanate groups, in particular by alkyl radicals.

An example of these aralkyl radicals is α,α-dimethylbenzyl.

Alkylene $R_3$ or $R_4$ is as a rule an alkylene group having 1 to 12 carbon atoms.

Examples of alkylene radicals are methylene, ethylene and tri-, tetra-, penta-, hexa-, hepta-, octa-, nona-, deca-, undeca- and dodecamethylene. Tetra-, hexa- and octamethylene are preferred.

An alkylene chain formed by two radicals $R_6$ together is as a rule tri- or tetramethylene.

Cycloalkylene $R_3$ or $R_4$ is as a rule a cycloalkylene group which has five or six ring carbon atoms and which may, if appropriate, also be part of an alkylene chain.

Examples of cycloalkylene radicals are cyclopentylene, cyclohexylene, methylcyclohexylene, 1,4-bis-methylene-cyclohexane and 3,5,5-trimethyl-3-methylene-cyclohex-1-yl.

Any alkyl radicals $R_5$ or $R_6$ are branched or in particular straight-chain radicals. The alkyl group in general contains one to twelve carbon atoms. Straight-chain alkyl radicals having one to six carbon atoms, in particular methyl radicals, are preferred.

Examples of alkyl radicals are methyl, ethyl, n-propyl, isopropyl, n-butyl, sec-butyl, tert-butyl, n-pentyl, n-hexyl, n-heptyl, n-octyl, 2-ethylhexyl, n-nonyl, n-decyl, n-undecyl and n-dodecyl.

Any alkenyl radicals $R_5$ are branched or in particular straight-chain radicals. Alkenyl radicals in general contain two to six carbon atoms. Examples of alkenyl radicals are vinyl, prop-1-enyl, prop-2-enyl, n-but-3-enyl, n-pent-4-enyl or n-hex-5-enyl. Straight-chain alkenyl radicals having two or three carbon atoms, in particular vinyl, prop-1-enyl or prop-2-enyl (allyl) are preferred.

Any cycloalkyl radicals $R_5$ or $R_6$ are in general groups having five to eight ring carbon atoms. Cyclohexyl is preferred.

Examples of cycloalkyl radicals are cyclopentyl, cyclohexyl, cycloheptyl and cyclooctyl.

Any aryl radicals $R_5$ are in general aromatic hydrocarbon radicals having six to fourteen, in particular six, carbon atoms. Examples of aryl radicals are phenyl, naphthyl, biphenyl and anthryl. Phenyl is preferred.

Any aralkyl radicals $R_5$ are as a rule groups having seven to twelve carbon atoms. Examples of aralkyl radicals are benzyl, α-methylbenzyl and α,α-dimethylbenzyl.

An m+n-valent radical $R_7$ of a polyisocyanate after removal of the isocyanate groups can in principle be any aliphatic, cycloaliphatic, aromatic or araliphatic radical.

In the context of this description, the term "polyisocanate" is also to be understood as meaning the term "polyisothiocyanate".

The polyisocyanate on which the radical $R_7$ is based can be a low molecular weight compound or a prepolymer. In the context of this description, "low molecular compound" is to be understood as meaning a compound having a molecular weight of less than about 1000. "Prepolymer" in the context of this description is to be understood as meaning a compound having a molecular weight (number-average) of about 1000 to 20,000.

The radical $R_7$ is derived, for example, from a low molecular weight aliphatic, cycloaliphatic, aromatic or araliphatic polyisocyanate which contains several, in particular two to about four, isocyanate groups per molecule, or from an adduct, containing isocyanate end groups, of such a polyiscyanate on compounds, in particular on prepolymer compounds, which contain several, in particular two to about four, groups containing active hydrogen atoms, such as amino, acid or in particular hydroxyl groups.

Examples of low molecular weight aliphatic radicals $R_7$ are alkylene radicals, in particular radicals having two to twelve C atoms, such as have already been described above.

Examples of low molecular weight cycloaliphatic radicals $R_7$ are cycloakylene radicals which have five or in particular six ring carbon atoms and can also be part of an alkylene chain, such as have already been described above.

Examples of low molecular weight aromatic radicals $R_7$ are arylene radicals, such as divalent aromatic hydrocarbon radicals having six to fourteen, in particular six, carbon atoms. Several such arylene radicals can also be joined to one another via bridge members, such as a direct C—C bond, —O—, —S— or —CH$_2$—. Examples of arylene radicals are 1,3- or 1,4-phenylene and methylene-bis-(phen-4-yl).

An example of a low molecular weight araliphatic radical $R_7$ is xylylene.

A radical of a prepolymeric polyisocyanate $R_7$ is derived, for example, from a prepolymeric polyester or polyether which contains hydroxyl end groups and in which the end groups are masked with a low molecular weight di- or triisocyanate. Examples of such prepolymers are given below.

One or more carbon atoms in the alkyl radicals $R_1$, $R_2$, $R_5$ and/or $R_6$ and/or in the alkylene radicals $R_3$, $R_4$ and/or $R_7$ can be replaced by oxygen atoms, so that polyalkylene glycol radicals occur. Examples of alkylene chains modified in this way are radicals which are derived from polyalkylene glycols. Examples of alkyl radicals modified in this way are derivatives which are derived from polyalkylene glycol monoalkyl ethers.

Examples of such radicals $R_3$ and $R_4$ are radicals of polyalkylene glycols containing monoamino end groups.

An alkylene radical $R_7$ in which one or more C atoms are replaced by O atoms is, for example, a polyoxyalkylene glycol radical, in particular a polyoxypropylene glycol radical or a polyoxybutylene glycol radical.

If one to three carbon atoms are replaced by oxygen atoms, sulfur atoms and/or nitrogen atoms in any cyclic radicals $R_1$ to $R_7$, the radicals can be aromatic or non-aromatic heterocyclic systems which are preferably five- or six-membered. In the case of heterocyclic systems, preferably one to three ring carbon atoms are replaced by nitrogen atom, or one or two ring carbon atoms are replaced by oxygen atoms or sulfur atoms. It is also possible for different hetero atoms to occur in one ring, for example a nitrogen atom and an oxygen atom.

The definition "one to three carbon atoms are replaced by oxygen atoms, sulfur atoms and/or nitrogen atoms" also includes those heterocyclic systems in which the ring hetero atoms, as well as being bonded into the ring system, also in turn carry additional atoms or substituents. Examples of such hetero groups are —NH— or —N(alkyl)—.

A cyclic radical $R_7$ in which one to three carbon atoms are replaced by oxygen atoms, sulfur atoms and/or nitrogen atoms is, for example, a radical of a triisocyanate which contains an isocyanurate ring, for example an N,N', N"-tris-(hexamethylene)-isocyanurate radical.

The radicals $R_3$ to $R_7$ are as a rule unsubstituted. However, they can also in turn carry substituents which are inert towards isocyanates.

Examples of substituents which are inert towards isocyanate groups are alkyl, alkenyl, alkoxy, alkylthio, cycloalkyl, aryl, aralkyl, cyano, carboxyalkyl and halogen.

Examples of alkyl, alkenyl, cycloalkyl, aryl and aralkyl groups are given above.

Any alkoxy or alkylthio substituents are branched or, in particular, straight-chain radicals. The alkyl group of these radicals in general contains one to twelve carbon atoms. Straight-chain alkyl radicals having one to six carbon atoms, in particular methyl radicals, are preferred.

Examples of alkoxy radicals are methoxy, ethoxy, n-propoxy, isopropoxy, n-butoxy, n-pentoxy and n-hexyloxy.

Examples of alkylthio radicals are methylthio, ethylthio, n-propylthio, isopropylthio, n-butylthio, n-pentylthio and n-hexylthio.

Any carboxyalkyl groups as substituents are, for example, those radicals which contain as alkyl groups the radicals listed above as examples of alkyl.

Any halogen substituents are, for example, fluorine, bromine or in particular chlorine.

$R_1$ is preferably a radical of the formula II.

$R_2$ is preferably hydrogen or a radical of the formula II.

$R_3$ is preferably $C_2$-$C_8$alkylene, and especially preferably pentylene.

$R_4$ is preferably $C_1$-$C_8$alkylene, which is unsubstituted or additionally carries one to three methyl substituents. $R_4$ is especially preferably propylene.

$R_5$ is preferably $C_1$-$C_4$alkyl or phenyl.

$R_6$ is preferably $C_1$-$C_4$alkyl, or two radicals $R_6$ together form a tri- or tetramethylene chain.

$R_7$ is preferably a radical of the formulae IVa to IVd

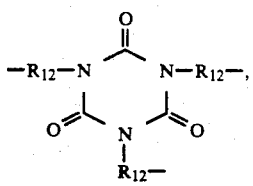
(IVa)

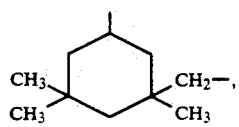
(IVb)

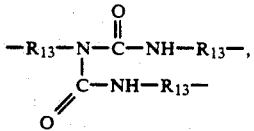
(IVc)

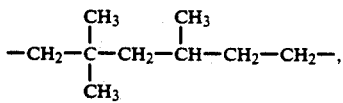
(IVd)

in which $R_{12}$ and $R_{13}$ are $C_2$-$C_{12}$alkylene, in particular hexamethylene.

Y is preferably —O—.

X is preferably —S—.

The index p is preferably 1 or in particular 0.

The index m is preferably 1.

The index n is preferably 2 to 5, or in particular 2.

Compounds of the formula Ib in which m is 1 and n is 2 are preferred.

Compounds of the formula Ia in which $R_1$ is a radical of the formula II, $R_2$ is hydrogen or a radical of the formula II, $R_3$ is $C_2$-$C_8$alkylene, $R_4$ is $C_1$-$C_8$alkylene which is unsubstituted or additionally carries one to three methyl substituents, $R_5$ and $R_6$ is $C_1$-$C_4$alkyl, Y is —O— and the index p is 1 or in particular 0 are particularly preferred.

Compounds of the formula Ib in which $R_1$ is a radical of the formula II, $R_2$ is hydrogen or a radical of the formula II, $R_3$ is $C_2$-$C_8$alkylene, $R_4$ is $C_1$-$C_8$alkylene which is unsubstituted or additionally carries one to three methyl substituents, $R_5$ and $R_6$ are $C_1$-$C_4$alkyl, $R_7$ is a radical of the formulae IVa to IVd, Y is —O—, X is —S—, the index p is 1 or in particular 0, the index m is 1 and the index n is 2 or in particular 1 are particularly preferred.

The compounds of the formula Ia or of the formula Ib can be prepared by reacting a mono-or polyisocyanate of the formula Va or Vb

(Va)

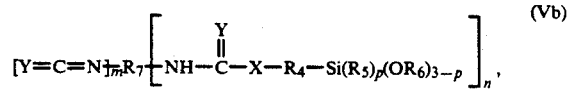
(Vb)

with a molar amount, corresponding at least to the number of isocyanate groups, of an imino alcohol of the formula VI

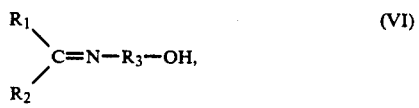
(VI)

in which $R_1$ to $R_7$, X, Y, m, n and p are as defined above.

The reaction is preferably carried out in an organic solvent which is inert towards both reaction partners, for example in an aromatic hydrocarbon, such as toluene. The reaction temperature is chosen from about 0° C. up to the reflux temperature of the particular solvent, depending on the reactivity of the starting substances.

The compounds of the formula Va are commercially available in some cases, or they can be prepared by phosgenation of aminosilanes which are known per se in a manner which is known per se.

The compounds of the formula Vb are likewise known per se. They can be obtained by reacting polyisocyanates which are known per se with less than the equivalent amount of aminosilanes, so that some of the isocyanate groups are retained for the subsequent reaction with the imino alcohol of the formula VI.

The compounds of the formulae Va and Vb are prepared, for example, by heating the two reaction partners, which are present as a solution in an inert organic solvent if appropriate, for example in an aromatic hydrocarbon, such as toluene. The reaction is in general carried out at elevated temperature, for example between 80° and 120° C.

The compounds of the formula VI are likewise known per se. They can be obtained by reacting aldehydes or ketones which are known per se, of the formula $R_1$—CO—$R_2$, in which $R_1$ and $R_2$ are as defined above, with an approximately equivalent amount of an amino alcohol which is known per se, of the formula $H_2N$—$R_3$—OH. The reaction is preferably carried out in an organic solvent which is inert towards both reaction partners, for example an aromatic hydrocarbon, such as toluene. The reaction is advantageously carried out at elevated temperature, for example between 80° and 120° C. The water of reaction formed is preferably removed azeotropically.

The compounds of the formula Ia and/or Ib can be employed as curing agents in polyurethane compositions, in particular in one-component formulations.

The invention thus also relates to curable compositions containing

A) an aliphatic, cycloaliphatic, aromatic or araliphatic compound having on average more than one isocyanate group per molecule and B) a compound of the general formula Ia and/or Ib.

All the polyisocyanates which are known per se can be employed as component A).

Component A) is as a rule the aliphatic, cycloaliphatic, aromatic or araliphatic compounds containing several, in particular about two to about four, isocyanate groups per molecule which have already been described above and on which $R_7$ is based.

Component A) in general contains a prepolymeric. This can be, for example, an adduct of polyisocyanates on a prepolymeric compound containing several, in particular two or three, groups having active hydrogen atoms, such as have already been described above for the preparation of the polyisocyanates on which $R_7$ is based. The term "polyisocyanate" also includes compounds containing groups derived from isocyanates which can be split again into isocyanate groups in the course of the curing reaction and then react like these. Examples of these groups are isocyanate groups blocked with phenols, lactams or ketoximes, uretdione groups or carbodiimide groups.

Examples of polyisocyanate prepolymers are compounds which are obtainable by masking prepolymers containing hydroxyl end groups, in particular polyesters or polyethers, with low molecular weight aliphatic, cycloaliphatic, aromatic or araliphatic poly-, in particular di- or triisocyanates. In this procedure, the masking component is introduced in excess, so that the product contains free isocyanate groups or groups which are derived from isocyanate.

Examples of low molecular weight polyisocyanates are m-phenylene diisocyanate, p-phenylene diisocyanate, 2,6-diisocyanatotoluene, 2,4-diisocyanatotoluene and industrial mixtures thereof with 2,6-diisocyanatotoluene, 1,5-diisocyanatonaphthalene, 4,4'-diisocyanatodiphenylmethane and industrial mixtures of various diisocyanatodiphenylmethanes (for example the 4,4'- and 2,4'-isomers), urethanized 4,4'-diisocyanatodiphenylmethane, carbodiimidized 4,4'-diisocyanatodiphenylmethane, the uretdione of 2,4-diisocyanatotoluene, triisocyanatotriphenylmethane, the adduct of diisocyanatotoluene and trimethylolpropane, the trimer of diisocyanatotoluene, diisocyanato-m-xylylene and N,N'-di-(4-methyl-3-isocyanatophenyl)-urea, co-trimerization products of diisocyanatotoluene and 1,6-diisocyanatohexamethylene, 1,6-diisocyanatohexane, cyclohexane 1,4-diisocyanate, 3,5,5-trimethyl-1-isocyanato-3-isocyanatomethylcyclohexane (isophorone diisocyanate), N,N',N''-tri-(6-isocyanatohexyl)-biuret, 2,2,4-trimethyl-1,6-diisocyanatohexane, 1-methyl-2,4-diisocyanatocyclohexane, 4,4'-bis-(isocyanato)-3,3'-dimethylbiphenyl, 4,4'-diisocyanatodicyclohexylmethane, trimeric isophorone diisocyanate, trimeric hexane diisocyanate and methyl 2,6-diisocyanatohexanoate. These compounds are known in the art of polyurethanes and most of them are commercially available.

Suitable prepolymeric polyesters containing hydroxyl end groups are derived from dicarboxylic acids and dialcohols.

Examples of dicarboxylic acids from which these polyesters are derived are saturated aliphatic dicarboxylic acids, such as succinic acid, adipic acid, sebacic acid or dimerized fatty acids, such as are commercially available, for example, under the name Pripol; or unsaturated aliphatic dicarboxylic acids, such as maleic acid; or cycloaliphatic dicarboxylic acids, such as hexahydrophthalic or tetrahydrophthalic acid; or aromatic dicarboxylic acids, such as phthalic, isophthalic or terephthalic acid.

Examples of dialcohols from which these polyesters are derived are compounds containing two alcoholic hydroxyl groups and/or phenolic hydroxyl groups in the molecule, such as aliphatic dialcohols, for example ethylene glycol, diethylene glycol and higher poly-(oxyethylene) glycols, propane-1,3-diol or higher poly-(oxypropylene) glycols, butane-1,4-diol or higher poly-(oxybutylene) glycols or hexane-1,6-diol; or cycloaliphatic dialcohols, such as 1,3- or 1,4-dihydroxycyclohexane or 1,4-cyclohexanedimethanol; or dialcohols containing aromatic groups, such as N,N-bis-(2-hydroxyethyl)-aniline; or mono- or polynuclear bisphenols, such as resorcinol, hydroquinone, bis-(4-hydroxyphenyl)-methane (bisphenol F), 2,2-bis-(4-hydroxyphenyl)-propane (bisphenol A) or bis-(4-hydroxyphenyl) ether.

The prepolymeric polyesters containing hydroxyl end groups can also be polylactones, for example the adduct of $\epsilon$-caprolactone on polyhydroxy or polyamine compounds.

Examples of prepolymeric polyethers containing hydroxyl end groups are polyalkylene glycols, in particular polypropylene glycols or polybutylene glycols having a functionality of two or three. These prepolymers are likewise known in the art of polyurethanes and most of them are commercially available.

To prepare the polyisocyanate prepolymers, the prepolymeric compounds containing the groups having active hydrogen atoms are reacted with the excess polyisocyanate in a manner which is known per se. If appropriate, the reaction is carried out in the presence of low molecular weight polyols or polyamines, in order to lengthen the chain in this manner. The proportions of reaction components are chosen here so that polyurethane prepolymers which preferably have an isocyanate content of about 1 to 10% by weight, based on the prepolymer, are formed. The reaction is preferably carried out in the presence of catalysts of urethane polymerization, such as Sn compounds, for example dibutyltin dilaurate.

About 0.1 to 20, in particular 1 to 10 parts by weight of component B) are usually employed per 100 parts by weight of component A).

The compositions according to the invention can be prepared by simply mixing the components on the equipment customary for this purpose.

If desired, the compositions according to the invention can be modified by auxiliaries or additives which are customary per se.

Examples of these are plasticizers, extenders, fillers and reinforcing agents, for example textile fibres, glass fibres, carbon fibres, mineral silicates, mica, quartz flour, hydrated aluminium oxide, bentonites, wollastonite, kaolin, silicic acid aerogel or metal powders, for example aluminium powder or iron powder, and furthermore pigments and dyes, such as carbon black, oxide colours and titanium dioxide, as well as flame-proofing agents, thixotropic agents, additional adhesion promoters, antioxidants and light stabilizers.

Organic carboxylic or sulfonic acids can furthermore be added to the compositions according to the invention in order to increase the rate of hydrolysis of the compounds of the formula Ia and Ib. About 1 to 10 meq of organic carboxylic or sulfonic acid are usually employed per equivalent of —C=N— group. Organotin compounds can furthermore also additionally be added to the compositions according to the invention.

The compositions according to the invention are distinguished by an increased storage stability in the absence of moisture.

Curing is in general effected by the action of moisture, in particular by atmospheric moisture. This in general takes place at room temperature, for example at temperatures between 20° and 40° C. If desired, curing can also be carried out in two stages by first allowing the composition to precure by storage in air and then proceeding with storage in water.

Coverings, coatings and adhesive bonds can be produced, in particular, with the compositions according to the invention. They are employed in the formulation suited to the particular specific field of use, for example as a paint or sealing, coating, casting, filling or gluing composition.

The compositions can be applied to a glass surface without the previously customary pretreatment with a primer, and produce coatings having excellent adhesion after curing.

The present invention likewise relates to the cured products obtainable from the compositions according to the invention and the use of the curable compositions for the abovementioned purposes.

The following examples illustrate the invention.

A. PREPARATION EXAMPLES

Example A1

Preparation of

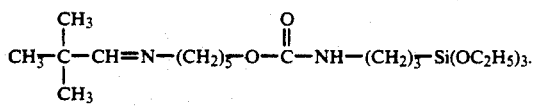

A1.1 Preparation of

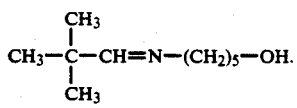

66.8 g (0.77 mol) of pivaldehyde are added to a suspension of 80 g (0.77 mol) of 5-amino-1-pentanol in 250 ml of toluene. The resulting solution is heated under reflux for 6 hours, using a water separator. The solvent is stripped off by means of a rotary evaporator and the residue is distilled (boiling point$_{50}$ mbar 120° C.). 107 g of a colourless liquid having the following analytical data are obtained:

$^1$H-NMR: d=7.49 (s, 1H), 3.66-3.29 (m, 5H), 1.74-1.23 (m, 6H) and 1.06 (s, 9H).

$^{13}$C-NMR (in CDCl$_3$): d=173.8, 62.0, 61.1, 35.9, 32.3, 30.4, 26.9 und 23.2.

| Elemental analysis | % C | % H | % N |
|---|---|---|---|
| Calculated | 70.12 | 12.36 | 8.18 |
| Found | 69.98 | 12.29 | 8.17. |

A1.2 Reaction of the Product from Example A1.1

A solution of 10 g (0.058 mol) of the product according to Example A1.1 in 20 ml of dry toluene is added to a solution of 16 g (0.058 mol) of isocyanatopropyltriethoxysilane in 20 ml of dry toluene. The solution is heated at 100° C. for one hour. The solvent is then stripped off in a rotary evaporator at 90° C. under 0.1 mbar and 25 g of a liquid having the following analytical data are obtained:

Viscosity (measured by the Epprecht method at 25° C.): 10,240 m.Pas.

$^1$H-NMR (in CDCl$_3$): d=7.49 (s, 1H), 4.98 (br, NH), 4.03 (t, J=6 Hz, 2H), 3.80 (q, J=7 Hz, 6H), 3.41-3.06 (m, 4H), 1.76-1.40 (m, 8H), 1.22 (t, J=7 Hz, 9H), 1.05 (s, 9H) and 0.70-0.53 (m, 2H).

$^{13}$C-NMR (in CDCl$_3$): d=171.8, 156.7, 64.5, 61.0, 58.3, 43.2, 35.8, 30.3, 28.7, 26.8, 23.2, 18.2 and 7.5.

| Elemental analysis | % C | % H | % N |
|---|---|---|---|
| Calculated | 57.38 | 10.11 | 6.69 |
| Found | 57.10 | 9.96 | 7.11. |

Example A2

Preparation of

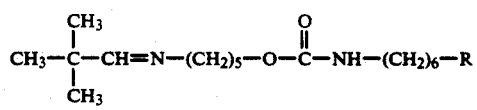

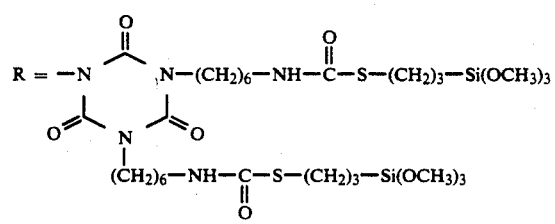

A mixture of 50 g (0.257 mol of NCO) of Desmodur ® N3200 (Bayer AG) [trimer of hexamethylene diisocyanate] and 33.7 g (0.171 mol) of 3-mercaptotrimethoxysilane is heated at 140° C. for one hour. The mixture is allowed to cool to 80° C. and a solution of 14.6 g (0.0857 mol) of the product from Example A1.1 in 100 ml of dry toluene is added dropwise. The mixture is heated at 80° C. for a further hour and the solvent is then stripped off in a rotary evaporator at 90° C. under 0.1 mbar. 98 g of a viscous material which chiefly has the above structure and has the following analytical data are obtained:

Viscosity (measured by the Epprecht method at 80° C.): 5120 m.Pas.

Imine content (titrimetric): 0.86 mol/kg (calculated: 0.87 mol/kg).

$^1$H-NMR (selected chemical shifts; in CDCl$_3$): d=7.49 (s, C$\underline{H}$=N), 5.90 (br, S—CO—N$\underline{H}$), 4.80 (br, O—CO—N$\underline{H}$), 3.56 (s, O—C$\underline{H}_3$) and 1.05 (s, C$\underline{H}_3$).

13C-NMR (selected chemical shifts; in CDCl3): d=172,0 (CH=N), 167.2 (S—CO—NH), 156.8 (O—CO—NH), 156.3 (isocyanurate ring), 50.4 (O—CH3), 26.8 (CH3) and 8.6 (Si—CH 2).

| Elemental analysis | % C | % H | % N | % S |
|---|---|---|---|---|
| Calculated | 51.71 | 8.40 | 9.18 | 6.00 |
| Found | 52.24 | 8.48 | 10.18 | 5.55. |

Example A3
Preparation of

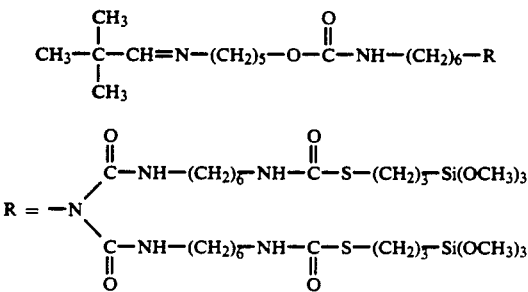

A mixture of 25 g (0.127 mol of NCO) of Desmodur ® N100 (Bayer AG) [biuret of hexamethylene diisocyanate] and 16.7 g (0.085 mol) of 3-mercaptopropyltrimethoxysilane is heated at 140° C. for one hour. The mixture is allowed to cool to 80° C. and a solution of 7.3 g (0.0425 mol) of the product from Example A1.1 in 50 ml of dry toluene is added dropwise. The mixture is heated at 80° C. for a further hour and the solvent is then stripped off in a rotary evaporator at 90° C. under 0.1 mbar. 48 g of a viscous material which chiefly has the above structure and has the following analytical data are obtained: Viscosity (measured by the Epprecht method at 80° C.): 20,480 m.Pas. Imine content (titrimetric): 0.80 mol/kg (calculated: 0.88 mol/kg).

1H-NMR (selected chemical shifts; in CDCl3): d=7.49 (CH=N), 3.55 (O—CH3) and 1.05 (CH3).

| Elemental analysis | % C | % H | % N | % S |
|---|---|---|---|---|
| Calculated | 51.84 | 8.80 | 9.40 | 6.15 |
| Found | 52.40 | 8.74 | 9.64 | 5.85. |

Example A4
Preparation of

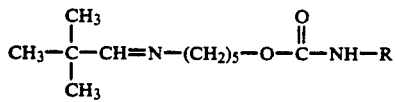

R =

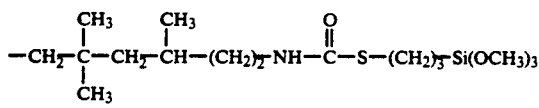

A mixture of 150 g (0.714 mol) of freshly distilled 1,6-diisocyanato-2,2,4-trimethylhexane and 104.2 g (0.714 mol) of 3-mercaptopropyltrimethoxysilane is heated at 140° C. for two hours. A solution of 11.8 g (0.029 mol) of this adduct is added dropwise to a solution of 5 g (0.029 mol) of the product from Example A1.1 in toluene and the mixture is heated at 100° C. for a further hour. The solvent is then stripped off in a rotary evaporator at 90° C. under 0.1 mbar. 16.4 g of a viscous liquid which chiefly consists of the adduct according to the above structure and has the following analytical data are obtained:

Viscosity (measured by the Epprecht method at 25° C.): 15,360 m.Pas.

1H-NMR (selected chemical shifts; in CDCl3): d=7.49 (s, CH=N), 3.56 (O—CH3) and 1.05 (CH3).

13C-NMR (selected chemical shifts; in CDCl·): d=171.9 (CH=N), 167.3 (S—CO—NH), 156.9 (O—CO—NH) and 8.5 (Si—CH2).

| Elemental analysis | % C | % H | % N | % S |
|---|---|---|---|---|
| Calculated | 56.12 | 9.59 | 7.27 | 5.55 |
| Found | 55.84 | 9.24 | 7.27 | 5.71. |

Example A5
Preparation of

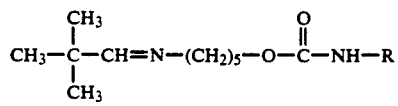

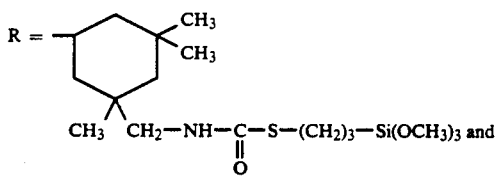

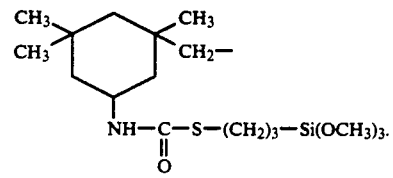

A mixture of 14.3 g (0.064 mol) of isophorone diisocyanate and 12.6 g (0.064 mol) of 3-mercaptopropyltrimethoxysilane is heated at 140° C. for one hour. The solution is allowed to cool to 80° C. and a solution of 11 g (0.064 mol) of the product from Example A1.1 in 20 ml of toluene is added dropwise. The mixture is heated at 80° C. for a further hour. The solvent is then stripped off in a rotary evaporator at 90° C. under 0.1 mbar. 37 g of a viscous liquid which chiefly consists of an adduct of the above structure and has the following analytical data are obtained:

Viscosity (measured by the Epprecht method at 80° C.): 7680 m.Pas.

1H-NMR (selected chemical shifts; in CDCl3): d=7.49 (s, CH=N), 3.56 (O—CH3) and 1.05 (CH3).

| Elemental analysis | % C | % H | % N |
|---|---|---|---|
| Calculated | 57.01 | 9.40 | 7.12 |
| Found | 57.24 | 9.60 | 6.94. |

B. USE EXAMPLES

Example B1

Preparation of a Polyurethane Prepolymer

A prepolymer containing isocyanate end groups is prepared by allowing a mixture of 531 g of dry polypropylene glycol containing bis-hydroxyl end groups and having a molecular weight of 2000 (Desmophen® 1900U from Bayer AG) and 0.3 ml of dibutyltin dilaurate to run into 150 g of methylenediphenyl diisocyanate (Isocyanate® M125 from Upjohn) at 80° C. in the course of one hour. 2.7 g of trimethylolpropane are then added and the mixture is stirred at 80° C. for a further two hours until a prepolymer containing isocyanate end groups and having an isocyanate content of 2.4% by weight has formed.

Examples B2-B6

Adhesion to Glass

5% of dry pyrogenic silicic acid (Aerosil® 380) and 5% of adhesion promoter according to the following Table 1 are added to the prepolymer obtained under Example B1. A polyurethane layer 5 mm thick is then cast on a glass plate. After storage in air for two weeks, these samples are stored in water at room temperature for two weeks. The results are compiled in Table 1. The symbols in the table have the following meanings:

(- -): the layer can easily be peeled off and the glass surface remains clean;

(-): the layer can be peeled off with difficulty and the glass surface remains clean;

(+ -): the majority of the layer can be removed by scratching with a knife;

(+): the majority of the layer remains stuck to the glass surface, in spite of scratching with a knife;

(+ +): the entire layer remains stuck to the glass surface, in spite of scratching with a knife.

TABLE 1

Composition and adhesion to glass of cured polyurethane prepolymers containing iminosilane adhesion promoter

| Example No. | Adhesion promoter according to Example No. | Result of the adhesion tests |
|---|---|---|
| B2 | A1.2 | (+ +) |
| B3 | A2 | (+ +) |
| B4 | A3 | (+ +) |
| B5 | A4 | (+) |
| B6 | A5 | (+) |
| without iminosilane adhesion promoter | | (- -) |

What is claimed is:

1. A compound of formula Ia or Ib

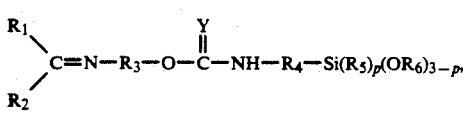  (Ia)

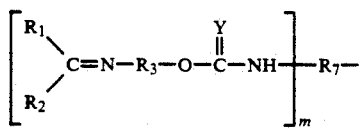  (Ib)

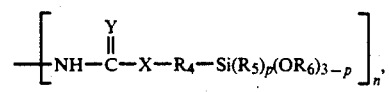

wherein $R_1$ is 1-methylcyclohex-1-yl, $\alpha,\alpha$-dimethylbenzyl or a radical of formula II

  (II)

in which $R_8$ and $R_9$ are identical or different $C_1$-$C_6$alkyl and $R_{10}$ is $C_1$-$C_{12}$alkyl, or $R_{10}$ is one of the radicals of the formulae IIIa, IIIb or IIIc $-O-R_{11}$, (IIIa)

  (IIIb)

  (IIIc)

in which $R_{11}$ is $C_1$-$C_{12}$alkyl, cyclohexyl, phenyl or benzyl, $R_2$ has the same meaning as $R_1$ or is hydrogen, or $R_1$ and $R_2$ together with the C atom to which they are bound are 2,2,6,6-tetramethylcyclohexyl, $R_3$ or $R_4$ is alkylene of 1 to 12 carbon atoms or cycloalkylene of 5 or 6 carbon atoms in the ring, 1,4-bismethylenecyclohexane or 3,5,5-trimethyl-3-methylenecyclohex-1-yl, $R_5$ is alkyl of 1 to 12 carbon atoms, alkenyl of 2 to 6 carbon atoms, cycloalkyl of 5 to 8 carbon atoms in the ring, aryl of 6 to 14 carbon atoms or aralkyl of 7 to 12 carbon atoms, $R_6$ is alkyl of 1 to 12 carbon atoms or cycloalkyl of 5 to 8 carbon atoms in the ring, or two radicals $R_6$ together are trimethylene or tetramethylene, $R_7$ is an m+n-valent linear or branched radical of a polyisocyanate after removal of the NCO groups, X is -S- or -NH-, Y is -O- or -S- p is 0, 1 or 2, m is 1 or 2, and n is an integer from 1 to 5.

2. A compound of the formula Ia or Ib according to claim 1, in which $R_3$ is $C_2$-$C_8$alkylene and $R_4$ is $C_1$-$C_8$alkylene which is unsubstituted or additionally carries one to three methyl substituents.

3. A compound of the formula Ia or Ib according to claim 1, in which $R_5$ is $C_1$-$C_4$alkyl or phenyl and $R_6$ is $C_1$-$C_4$alkyl, or two radicals $R_6$ together form a tri- or tetramethylene chain.

4. A compound of the formula Ib according to claim 1, in which $R_7$ is a radical of the formula IVa to IVd

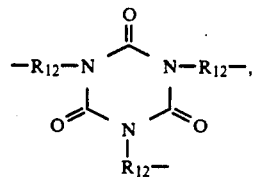 (IVa)

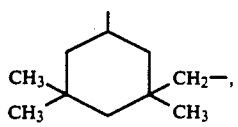 (IVb)

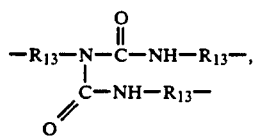 (IVc)

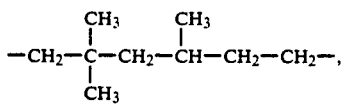 (IVd)

in which $R_{12}$ and $R_{13}$ are $C_2$-$C_{12}$alkylene.

5. A compound of the formula Ia or Ib according to claim 1, in which Y is —O—, X is —S—, p is 1 or 0, m is 1 and n is 2 to 5.

6. A compound of the formula Ib according to claim 1, in which m is 1 and n is 2.

7. A compound of the formula Ia according to claim 1, in which $R_1$ is a radical of the formula II, $R_2$ is hydrogen or a radical of the formula II, $R_3$ is $C_2$-$C_8$alkylene, $R_4$ is $C_1$-$C_8$alkylene which is unsubstituted or additionally carries one to three methyl substituents, $R_5$ and $R_6$ are $C_1$-$C_4$alkyl, Y is —O— and p is 1 or 0.

8. A compound according to claim 5 wherein p is 0 and n is 2.

9. A compound according to claim 7 wherein p is 0.

10. A compound of formula Ib according to claim 1 in which
$R_1$ is a radical of formula II,
$R_2$ is hydrogen or a radical of formula II,
$R_3$ is $C_2$-$C_8$alkylene,
$R_4$ is $C_1$-$C_8$alkylene which is unsubstituted or additionally carries one to three methyl substituents,
$R_5$ and $R_6$ are $C_1$-$C_4$alkyl,
$R_7$ is a radical of formula IVa, IVb, IVc or IVd

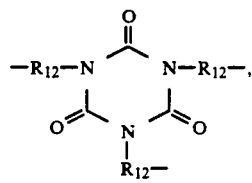 (IVa)

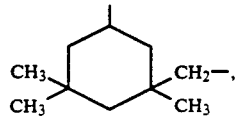 (IVb)

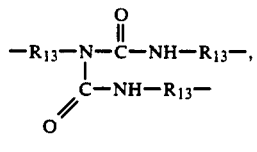 (IVc)

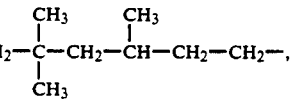 (IVd)

in which $R_{12}$ and $R_{13}$ are $C_2$-$C_{12}$alkylene,
Y is —O—,
X is —S—,
p is 0 or 1,
m is 1, and
n is 1 or 2.

11. A compound according to claim 10 wherein p is 0 and n is 1.

* * * * *